United States Patent
Yamaguchi et al.

(10) Patent No.: US 7,250,155 B2
(45) Date of Patent: Jul. 31, 2007

(54) DENTAL BLEACHING AGENT KIT AND THE METHOD FOR BLEACHING TEETH

(75) Inventors: Shin Yamaguchi, Tokyo (JP); Toshihiro Sekiguchi, Tokyo (JP); Keisuke Ikushima, Tokyo (JP); Shoji Akahane, Tokyo (JP); Koyu Aoki, Aichi-gun (JP); Takeshi Morikawa, Seto (JP); Takeshi Ohwaki, Nagoya (JP); Yasunori Taga, Nagoya (JP)

(73) Assignees: GC Corporation, Tokyo (JP); Kaisha Toyota Chuo Kenkyusho, Aichi-gun (JP)

( * ) Notice: Subject to any disclaimer, the term of this patent is extended or adjusted under 35 U.S.C. 154(b) by 238 days.

(21) Appl. No.: 10/791,783

(22) Filed: Mar. 4, 2004

(65) Prior Publication Data

US 2004/0180008 A1   Sep. 16, 2004

(30) Foreign Application Priority Data

Mar. 10, 2003  (JP)  ............... 2003-062839

(51) Int. Cl.
*A61K 8/00* (2006.01)
*B01J 27/24* (2006.01)
*B01J 21/06* (2006.01)

(52) U.S. Cl. .............. 424/53; 424/53; 433/216; 502/350; 502/200

(58) Field of Classification Search ............ None
See application file for complete search history.

(56) References Cited

U.S. PATENT DOCUMENTS 5,766,574 A * 6/1998 Christina-Beck et al. ..... 424/53
6,162,055 A * 12/2000 Montgomery et al. ...... 433/216
6,343,933 B1   2/2002 Montgomery et al.
6,387,844 B1 * 5/2002 Fujishima et al. .......... 502/350
2002/0006865 A1 * 1/2002 Morikawa et al. .......... 502/200
2003/0103913 A1 * 6/2003 Nathoo ..................... 424/53
2003/0198605 A1 * 10/2003 Montgomery ............... 424/53

FOREIGN PATENT DOCUMENTS

| EP | 1 048 291 | 11/2000 |
| EP | 1 192 933 | 4/2002 |
| EP | 1 250 896 | 10/2002 |
| EP | 1 393 711 | 3/2004 |
| WO | WO 02/060401 | 8/2002 |

OTHER PUBLICATIONS

Wikipedia, the free encyclopedia, Titanium Dioxide, http://en.wikipeida.org/wiki/Titanium_dioxide.*

* cited by examiner

*Primary Examiner*—Frederick Krass
*Assistant Examiner*—Lezah Roberts
(74) *Attorney, Agent, or Firm*—Oblon, Spivak, McClelland, Maier & Neustadt, P.C.

(57) ABSTRACT

To eliminate a defect in conventional dental bleaching agent, that light for activating titanium oxide hardly reaches down to the titanium oxide at the teeth surface to be bleached, a dental bleaching agent set consists of two components of which the first component is attached to teeth surface and irradiation of light is followed after the second component is contacted on the teeth surface, the first component consisting of an organic solvent, containing at least one of a titanium oxide, a nitrogen doped titanium oxide, and a titanium oxinitride having photocatalytic activities, and preferably one or more of a metal oxide, a metal salt, and a metal powder, a thickener and water, the second component consisting of a compound that produces hydrogen peroxide in water, a thickener and a carrier.

13 Claims, No Drawings

DENTAL BLEACHING AGENT KIT AND THE METHOD FOR BLEACHING TEETH

BACKGROUND OF THE INVENTION

1. Field of the Invention

The present invention relates to a teeth-bleaching set and the method for using such a teeth-bleaching set in removing (bleaching), by employing photocatalytic and hydrogen peroxide reactions, coloration and discoloration of teeth resulting from the deposition of pigments on the teeth.

2. Description of Conventional Art

Generally, whiteness of teeth is an important cosmetic element desired especially by young women and cases of seeking treatments for having whiter teeth increase. A method commonly in use is to use hydrogen peroxide solution.

In other words, in a common teeth-bleaching method, hydrogen peroxide with light or heat is utilized. In this method, a piece of gauze impregnated with hydrogen peroxide solution is placed on the labial surface of the teeth, and is irradiated, from side to side, with a lamp for about 30 minutes. This requires that the lamp used must be kept as close to the teeth as possible, and the hydrogen peroxide solution must be replenished approximately every five minutes to keep the gauze moist.

There is also a method, in which the irradiation of light from a lamp is replaced by applying a high frequency current for one (1) second with a high frequency electric cautery knife equipped with a spoon-shaped tip, then pausing for eight (8) seconds, and repeating this process for 6~8 times. In yet another method, in place of a piece of gauze impregnated with hydrogen peroxide solution, a solution (paste) made by mixing a thickener with hydrogen peroxide solution is used as an agent, and is applied directly to the teeth surface.

Besides the above, there are numerous bleaching agents and methods that have been proposed in using combinations of hydrogen peroxide solution, a variety of instruments, and other agents. Among them are: a bleaching method in which a mixture of hydrochloric acid, hydrogen peroxide solution, and diethylether is used as a bleaching agent; a method in which a paste made from kneading together sodium perborate powder and 30% by weight of hydrogen peroxide solution is used as a bleaching agent; a bleaching agent in which a mixture of hydrogen peroxide solution with orthophosphoric acid is used and a bleaching method with using it, as seen in Japanese Patent Laid-Open JP-A-08143436; a bleaching agent made by a mixture of anhydrous silicic acid with hydrogen peroxide solution and a method of bleaching a vital teeth by application of said bleaching agent, as seen in Japanese Patent Laid-Open JP-A-05320033; and dental bleaching compositions made from a dental bleaching agent (such as urea hydrogen peroxide, hydrogen carbamide peroxide and carbamide peroxide.) and a matrix material (such as carboxymethylene.), and their respective application methods, as seen in Japanese Patent Laid-Open JP-A-08113520, etc. But these conventional methods that employ hydrogen peroxide have a common shortcoming in that they require a lengthy bleaching time. Also, there is a bleaching method practiced in the United States in which urea peroxide of about 10% by weight concentration is used instead of hydrogen peroxide, but due to lengthy time required as in the use of hydrogen peroxide, the results are not satisfactory.

Instead of using hydrogen peroxide solution in bleaching as mentioned above, a dental bleaching method by using a titanium dioxide powder having photocatalytic activities and hydrogen peroxide in low concentration has been proposed, as seen in Japanese Patent Laid-Open JP-A-11092351. However, the conventional bleaching agent employing the titanium dioxide has a poor bleaching efficiency and, in order to meet the satisfactory whitening demanded by patients, a lengthy bleaching time is also needed.

SUMMARY OF THE INVENTION

An objective of the present invention is to provide a dental bleaching agent set and an accompanying dental bleaching method by which the shortcomings associated with the conventional techniques are removed, and thus a higher bleaching efficiency is achieved.

As a result of the earnest investigations made by the present inventors in solving the problems mentioned above, the inventors found that, when the external light activates the conventional bleaching agent that contains approximately 5% by weight of titanium oxide powder having photocatalytic activities, the light is difficult to reach to the teeth surface where the bleaching action is to take place, due to the sheltering effects of the titanium oxide itself, and hence the bleaching efficiency becomes low. Focusing on this, a new dental bleaching agent set that activates the titanium oxide more efficiently, and the method for applying this bleaching agent is thus completed.

In particular, one aspect of the present invention is a dental bleaching agent set that is characterized by having two components of a first component for previously attaching to a tooth surface comprising an organic solvent containing at least one of a titanium oxide powder, a nitrogen doped titanium oxide powder, and a titanium oxinitride powder having photocatalytic activities and a second component for contacting to the tooth surface comprising a compound that produces hydrogen peroxide in water, a thickener and a carrier. In the first component, it is preferred to have 0.001~30% by weight of at least one of the titanium oxide powder, a nitrogen doped titanium oxide powder, and a titanium oxinitride powder having photocatalytic activities, and it is preferable that the first component also contains at least one of a metal oxide, a metal salt, and a metallic powder in the range of 0.001~10% by weight. In addition, in some cases, 0.5~20% by weight of a thickener and/or water are contained in the first component. It is preferable that the second component has the following composition: a compound that produces hydrogen peroxide in water: 1~40% by weight; a thickener: 0.5~20% by weight, and a carrier: the balance.

For the titanium oxinitride powder having photocatalytic activities, which is contained in the first component, it is preferred to have a Ti—O—N structure containing nitrogen in its crystalline lattices and exhibit photocatalytic activities in the visible spectral region. It is further preferred that it carries on its surface, ceramics in an island form, an acicula form, or a mesh form, and also carries a charge separation substance for an increased efficiency.

Also, it is preferred that a pH value is 5.0~10.0 for the first component and/or the second component, so that the hydrogen peroxide producing compound contained in the second component can be used at a range of high activities.

The other item that is related to the present invention is a dental bleaching method characterized by attaching, on the teeth surface, the first component comprising an organic solvent containing at least one of a titanium oxide powder, a nitrogen doped titanium oxide powder, and a titanium oxinitride powder having photocatalytic activities, followed by an irradiation with light after the second component, containing a compound producing hydrogen peroxide in water, a thickener, and a carrier, is brought to contact to the teeth surface. Specifically, it is preferable that the first component comprising an organic solvent containing 0.001~30% by weight of at least one of a titanium oxide powder, a nitrogen doped titanium oxide powder, and a titanium oxinitride powder having photocatalytic activities, and 0.001~10% by weight of one or more of a metal oxide, a metal salt, and a metallic powder, is attached to the teeth surface. It is then irradiated with light after the second component comprising 1~40% by weight of a compound that produces hydrogen peroxide in water, 0.5~20% by weight of a thickener, and a carrier; is brought to contact on the teeth surface.

DESCRIPTION OF THE PREFERRED EMBODIMENTS

Concerning the titanium oxide powder having photocatalytic activities that is used in the dental bleaching agent set and the bleaching method of the present invention, even though any conventionally used titanium oxide powder, be it an antase type, a rutile type or a brookite type, can be used irrespective of its form or characteristics so long as they have photocatalytic activities, but the anatase type titanium oxide powder is preferred. And, the titanium oxinitride powder that has a Ti—O—N structure containing nitrogen in the crystalline lattices of titanium oxide is preferably used. With regard to the titanium oxinitride powder, it is preferred that it has the same Ti—O—N structure as in the titanium oxide which contains nitrogen in its crystalline lattices, as shown in WO01/10552, and also exhibits photocatalytic activities in the visible spectral region.

The aforementioned titanium oxinitride powder can be made, for example, by heating titanium oxinitride or titanium oxide hydrates under ammonia-containing atmosphere, nitrogen gas-containing atmosphere, or nitrogen and hydrogen gas mixture-containing atmosphere, as is shown in WO01/10552. Further, as is shown in JP-A-2002-154823, the titanium oxinitride powder can also be obtained by heating a mixture of titanium oxide powder and urea; and the titanium oxide powder that does not contain nitrogen on the outer surface can also be used.

Also, for at least one of the titanium oxide powder, the nitrogen doped powder, and the titanium oxinitride powder having photocatalytic activities to be used in the present invention, a powder made in the following methods can also be used as is shown in JP-A-2001-205104. The powder with its titanium replaced by one or more among vanadium, chromium, manganese, iron, cobalt, nickel, copper, zinc, ruthenium, rhodium, rhenium, osmium, palladium, platinum, iridium, niobium, molybdenum. And for the nitrogen doped titanium oxide, it is formed by doping one or more of those metals between the crystalline lattices of titanium oxide, or, in the case of a titanium oxide polycrystalline aggregate, doping them at the crystal boundaries.

As for at least one of the titanium oxide, the nitrogen doped titanium powder, and the titanium oxinitride powder for the use in the present invention, the powder may carry ceramics on its surface in an island form, an acicula form, or a mesh form. The ceramics can be chosen, for example, from at least one or more among alumina, silica, zirconia, magnesia, calcia, calcium phosphate, apatite, amorphous titanium oxide, and fluorine resin. These ceramics can easily absorb the deposited pigments on the teeth, and hence enhance the whitening power.

Also, the aforementioned at least one of the titanium oxide powder, the nitrogen doped titanium oxide powder, and the titanium oxinitride powder having photocatalytic activities may carry charge separation materials. The charge separation materials can be selected, for example, from one or more among Pt, Pd, Ni, $RuO_x$, $NiO_x$, $SnO_x$, $Al_xO_y$, and $ZnO_x$. These charge separation materials can effectively prevent the recombination of electrons and positive holes by capturing electrons or positive holes, and therefore, allow the photocatalytic reaction to proceed more effectively, thereby improving the whitening efficiency.

As to the particle diameter of at least one of the titanium oxide powder, nitrogen doped titanium oxide powder, and the titanium oxinitride powder having the photocatalytic activities, although a suitable diameter range is 1~500 nm, the range of 5~200 nm is preferred. As to the proper amount of the powder having the photocatalytic activities in the first component, even though a small amount will be quite effective, yet a insufficient amount will sometime require, depending on the degree of discoloration of the teeth, a lengthy time in obtaining the desired results. On the other hand, an excessive quantity of the powder will, due to its own property of sheltering from light, possibly lower the whitening effectiveness. Therefore, the quantity of the powder in the first component is preferred to be 0.001~30% by weight, or better at 0.001~10% by weight, or even better at 0.01~2% by weight.

In the dental bleaching agent set and dental bleaching method of the present invention, it is necessary to use an organic solvent to enhance the attachment, to the teeth surface, of the first component that contains at least one of the titanium oxide powder, the nitrogen doped titanium oxide powder, the titanium oxinitride powder having photocatalytic activities. From the operational perspective of attachment to the teeth surface, the preferred solvents are, for example, alcohols such as ethanol, glycerin, ethylene glycol, diethylene glycol, and propylene glycol, or polyhydric alcohols. Among the polyhydric alcohols, for example, polyethylene glycol, polypropylene glycol, sorbitol, mannitol by themselves or their mixtures are preferred for their superior safety and excellent affinity to the teeth.

Concerning the first and the second components of the present invention of the dental bleaching agent set and dental bleaching method, it is preferred that the pH value is adjusted to a range of 5.0~10.0. This is to improve the activity level of the compound that produces hydrogen peroxide in water, present in the second component applied to teeth after the first component. If the pH value is less than 5.0, the dentin is liable to be decalcified, and if higher than 10.0, the proteins in the dentin are liable to be denatured.

According to the present invention of the dental bleaching agent set and the dental bleaching method, it is preferable to incorporate one and more of a metal oxide, a metal salt, and a metal powder in the first component, in order to improve the activities of the compound that produces hydrogen peroxide in water and is contained in the second component subsequently applied. The incorporation of one or more of the metal oxide, a metal salt, and a metal powder must be in the first component instead of the second component, in order to avoid a vigorous reaction that will occur between these and the compound producing hydrogen peroxide in water that is contained in the second component. As to the metal oxide, the metal salt, and the metal powder, there is no special limitation so long as they react with the compound that produces hydrogen peroxide in water. However, the preferred metal oxide are manganese oxide, platinum oxide, ruthenium oxide, titanium oxide, and iron oxides. Among the preferred metal salts that can be cited are aluminum chloride, aluminum acetate, aluminum salicylate, aluminum acrylate, aluminum hydroxide, aluminum nitrate, aluminum carbonate, aluminum lactate, aluminum sulfate, itaconic acid aluminum, aluminum phosphate, aluminum polychloride, aluminum iodide, iron chloride, iron sulfate, iron nitrate, iron hydroxide, iron ammonium sulfate, iron citrate, iron succinate, iron bromide, iron phosphate, iron dichloride, iron ethylene diamine, iron oxalate, tin chloride, tin acetate, tin phosphate, tin diphosphate. Under a certain circumstance, two or more of the above compounds may be used. As to the metal powder, the powders of platinum, gold, ruthenium, various stainless steel, and titanium are preferred. A suitable average diameter of these powder particles is 1~500 nm, and a range of 5~200 nm is preferred. As to the proper quantity of these powder particles in the first component, 0.001~10% by weight is suitable, and 0.001~5% by weight is preferred, and 0.01~1% by weight is even more preferable. Even the presence of a small quantity of these powder particles will show its effectiveness, but with an insufficient quantity, it is liable not to improve the bleaching effects. On the other hand, when an excessive quantity of these powder particles is used, it is liable not to achieve effective whitening of the teeth due to the excessive thickness of film that is formed on the teeth surface.

In the first component of the dental bleaching agent set and the method of the dental bleaching of the present invention, in order to make the powder having photocatalytic activities stay on the teeth surface effectively, and to improve the ease in applying it to teeth, it is preferable to further contain 0.5~20% by weight of a thickener. When the quantity of the thickener is below 0.5% by weight, it is difficult to realize the effect of a thickener, and when it exceeds 20% by weight, it is liable to cause difficulties in application due to solution's excessively high viscosity. As to the thickener, there is no especial limitation on those that are used in traditional dentistry, and a wide variety of synthetic, natural and inorganic thickeners can be used. Among synthetic thickeners that can be used are cellulose sodium glucolate, sodium alginate, alginic acid propylene glycol ester, carboxy polymethylene, sodium carboxymethyl cellulose, calcium carboxymethyl cellulose, methyl vinylether/anhydrous maleic acid, starch sodium glycolate, starch sodium phosphate ester, sodium polyacrylate, methyl cellulose, hydroxy propylcellulose, and polyvinyl pyrrolidone. Among natural thickeners that can be used are guar gum, bean gum, tara gum, tamarind seed gum, gum arabic, tragant gum, karaya gum, alginic acid, carageenan, xanthan gum, gellan gum, curdlan, chitin, chitosan, and chitosamine. Among inorganic thickener that can be used are calcium carbonate, calcium silicate, magnesium silicate, sodium magnesium silicate, silica powder, amorphous hydrous silicic acid, and fumed silica. It has been confirmed from experiments that a suitable viscosity range obtained with the thickener is 0.2~30 Pa·s (25° C.). The quantity of the thickener needed to reach this viscosity range is depending on the thickener used, and, therefore, the suitable quantity is determined on an individual basis.

According to the present invention of the dental bleaching agent set and the dental bleaching method, water is sometime added to the first component based on the consideration of the reactivity of the powder having the photocatalytic activities. The quantity of water that is mixed into the first component is preferably 1~30% by weight. If it is less than 1% by weight, at least one of the titanium oxide powder, the nitrogen doped titanium powder, and titanium oxinitride powder will not react sufficiently, and for over 30% by weight, the first component tends to hardly dry on the teeth surface.

According to the present invention of the dental bleaching agent set and the dental bleaching method, there is no special limitation for a compound producing hydrogen peroxide in water, that is contained in the second component, so long as it can produce hydrogen peroxide in an aqueous solution. For example, hydrogen peroxide, perborate, percarbonate, perphosphate, persulfates, calcium peroxide, magnesium peroxide, and urea peroxide can be cited, but hydrogen peroxide and urea peroxide are preferred. It is preferable for the second component to contain 1~40% by weight of these compounds that produce hydrogen peroxide in water, and it is even more preferable to contain 1~15% by weight. If the second component contains the compound producing hydrogen peroxide in water less than 1% by weight, it is difficult to achieve whitening effects, and for more than 40% by weight, the improvement in whitening effects is hardly noticeable while compromising the safety.

According to the present invention of the dental bleaching agent set and the dental bleaching method, it is necessary to add a thickener to the second component containing a compound that produces hydrogen peroxide in water, in order to make the compound stay effectively on the teeth surface and for the ease in application, and the quantity of the thickener therein is preferred to be 0.5~20% by weight. If it is less than 0.5%, the effect of adding a thickener is hard to be achieved, and for more than 20% by weight, the viscosity is too high for an easy application onto the teeth surface. As to the thickeners, those aforementioned thickeners that can be mixed in the first component can also be used. According to the experiments, the viscosity with the addition of the thickener is preferred to be 0.2~30 Pa·s (25° C.), the same as the first component with a suitable thickener added.

According to the present invention of the dental bleaching agent set and the dental leaching method, it is necessary to incorporate, in the second component, a carrier as a basic ingredient for stabilizing and dispersing the compound that produces hydrogen peroxide in water. By incorporating a carrier, or a combination of carriers thereof, in accordance with the thickeners described above, it is possible to adjust the concentration of the chosen compound that produces hydrogen peroxide in water, and the viscosity of the second component. As to the carrier, water, sorbitol, glycerol, stearyl alcohol, glycerin, ethylene glycol, diethylene glycol, polyethylene glycol, propylene glycol, polypropylene glycol, mannitol, and other polyols can be used.

It is of course possible to contain, to the extent not to lower the effectiveness of the first and the second components according to the present invention of the dental bleaching agent set and the dental bleaching method, ordinary additives such as sweeteners, fragrances, preservatives and stabilizers.

In performing the dental bleaching method in accordance with the present invention, the first component, consisting of an organic solvent and at least one of the titanium oxide powder, the nitrogen doped titanium oxide powder, and the titanium oxinitride powder having photocatalytic activities, is attached to the teeth surface first. The easiest way of attaching a layer of the first component to the teeth surface is by applying it directly on the teeth surface with a brush or the like.

It is then followed by bringing the second component, containing a thickener, a carrier, and a compound that produces hydrogen peroxide in water, to contact to the teeth surface. The easiest method of contacting this second component to the teeth surface is by directly applying it on the teeth surface with a brush or the like as done for the first component. Other methods include impregnating the second component in a sufficiently translucent material, such as cloths, papers, glass cloths, ceramic papers, organic gels, inorganic gels, and bring it to a contact at the teeth surface. Another method is by keeping the second component in a suitable and sufficiently translucent resin retainer in the shape of a mouth guard, then followed by a proper and suitable method in bring the second component to contact to the teeth or teeth raw surface where the first component was already attached. And subsequently, irradiation of light is performed.

For the light source (irradiation equipment) to be used in performing the dental bleaching method of the present invention, in general, the use of incandescent lights, fluorescent lights, halogen lamps, xenon lamps, mercury lamps, and UV lamps can be cited. But from the viewpoint of safety, convenience, and the whitening effects, LED (light emitting diode) and semiconductor lasers are especially preferred. As to the irradiating light, it is desirable, from the viewpoint of production of the active oxygen, via photocatalytic reaction arising from the photocatlytic activities of the powder, and its subsequent oxidation reaction, a light that is abundant in energetic short wave such as the ultraviolet light is preferred. But the ultraviolet light is harmful in causing inflammation and cancers in human body, and, therefore, from the viewpoint of safety, the use of a visible light, especially with energetic violet and/or blue lights, is preferable.

The dental bleaching method of the present invention is performed by a sequential steps of attaching the first component to the teeth surface, followed by contacting the second component on the first component, and then irradiating light. These sequential steps of treatment can be repeated several times. As to the number of applications required of these sequential steps of attachment, contacting, and irradiation by light, it is adjusted according to the degree of discoloration of the teeth. In practice, generally the dental bleaching set applied on teeth surface is replaced by a new one in about 5~20 minutes, and such interval and frequency are determined according to the condition of the teeth, the type and the concentration of the compound used in generating oxygen in water. The dental bleaching agent set and dental bleaching method of the present invention is effective in whitening both demyelinated and myelinated teeth, safely and conveniently, and, above all, with remarkable results.

EXAMPLES

The present invention will be explained next with the following examples, but it is not to be construed as the limitation of the present invention.

<Production of the first component>

As shown in Tables 1~2, added, while stirring, into one or more of organic solvents such as ethanol, glycerin, polyethylene glycol (average molecular weight 200), were the titanium oxide powder or the titanium oxinitride powder having the photocatalytic activities, and, as needed, a metal powder such as platinum powder or iron chloride. After their dispersal, thickeners, such as sodium magnesium silicate or silica fine powder (trade name: Aerosil R972, manufactured by Nippon Aerosil Co., Ltd.) was added little by little, as needed, to produce the first component of the dental bleaching agent set. The product was then sealed in a light shading container.

For the titanium oxide powder or titanium oxinitride powder, the following were used.

<Powder A>

A commercially available titanium dioxide powder (Trade name: ST-01, manufactured by Ishihara Sangyo Kaisha, Ltd) is used.

<Powder B>

For the titanium oxinitride powder having a Ti—O—N structure, the following were used. Produced by heating, at 450° C. for 30 minutes, a mixture of urea and a commercially available titanium dioxide powder (Trade name: ST-01, manufactured by Ishihara Sangyo Kaisha, Ltd), as shown in JP-A-2002-154823.

<Powder C>

For the titanium oxinitride powder having a Ti—O—N structure, the following were used. Produced by heating, at 600° C. for 3 hours and under the atmosphere of argon and ammonia gas mixture, a commercially available titanium dioxide powder (Trade name: ST-01, manufactured by Ishihara Sangyo Kaisha, Ltd), as shown in WO01/10552.

<Powder B-Ap>

Produced by supporting apatite on the surface of the aforementioned powder B by the method shown in WO01/10552.

<Powder C-Pt>

Produced by supporting platinum on the surface of the aforementioned powder C by the method shown in JP-A-2001-205103.

<Production of the second component>

As shown in Table 3, a carrier was made from one or more of polypropylene glycol, polyethylene glycol, and glycerin, and water. Then the following were added to the carrier to produce the second component of the dental bleaching agent set: hydrogen peroxide and/or urea peroxide as the compound for producing hydrogen peroxide in water; and one or both of sodium magnesium silicate and silica fine powder (trade name: Aerosil R972, manufactured by Nippon Aerosil Co., Ltd.) and carboxy polymethylene (trade name: Carbopol 940, manufactured by BF Goodrich, Co.) as a thickener.

In the following Examples, the combinations among a variety of aforementioned first component, labeled from 1~10, and that of the second component, labeled from 1~4, are shown.

In particular, the combinations between the second component 1 and each of the first component 1~5 are shown in the Examples 1~5. The combinations between the second component 2 and each of the first component 6~10 are shown in the Examples 6~10. The combinations between second component 3 and each of the first component 1~10 are shown in Examples 11~20. The combinations between the second component 4 and each of the first component 1~10 are shown in the Examples 21~30. For the second component 4, two solutions with a volume ratio of 1:1 were mixed immediately before use. The Comparative Example 1 which serves as the composition representing the conventional dental bleaching agent is a mixture of 3% by weight of titanium dioxide powder (Trade name: ST-01, manufactured by Ishihara Sangyo Kaisha, Ltd.) and 10% by weight of hydrogen peroxide in water; while the Comparative Example 2 is prepared by adding enough water to 9.94 g of hydrogen peroxide, 0.60 g of phosphoric acid, and 2.00 g of sodium pyrophosphate ten hydrates to make a total weight of 60 g.

TABLE 1

(% by weight)

| | first component 1 | first component 2 | first component 3 | first component 4 | first component 5 |
|---|---|---|---|---|---|
| powder A | 5 | | | 7 | |
| powder B | | 2 | | | 1 |
| powder C | | | 2.5 | | |
| water | 30 | 25 | 25 | | 25 |
| ethanol | 61 | 10 | | | |
| glycerin | | 59.95 | 69.5 | 38 | |
| polyethylene glycol | | | | 53 | 71.95 |
| platinum powder | | 0.05 | | | 0.05 |
| iron chloride | 1 | | 1 | | |
| sodium magnesium silicate | 3 | 3 | | | |
| silica fine powder | | | 2 | 2 | 3 |
| total | 100 | 100 | 100 | 100 | 100 |

TABLE 2

(% by weight)

| | first component 6 | first component 7 | first component 8 | first component 9 | first component 10 |
|---|---|---|---|---|---|
| powder B-Ap | 1.5 | 2 | 4 | | |
| powder C-Pt | | 3 | | 5 | 5 |
| water | | | | 10 | 5 |
| ethanol | 95 | 85 | 83.5 | 70 | 80 |
| glycerin | | 8 | | | |
| polyethylene glycol | | | 10 | 14 | |
| platinum powder | 0.5 | | 0.5 | | |
| iron chloride | | | | | 2 |
| sodium magnesium silicate | 3 | 2 | 2 | 1 | 4 |
| silica fine powder | | | | | 4 |
| total | 100 | 100 | 100 | 100 | 100 |

TABLE 3

(% by weight)

| | second component 1 | second component 2 | second component 3 | second component 4 | |
|---|---|---|---|---|---|
| polypropylene glycol | | 40 | | | |
| polyethylene glycol | | | 10 | | |
| glycerin | 16.5 | 14 | 20 | 76.5 | |
| water | 60 | 10 | 31.5 | | 61.5 |
| hydrogen peroxide | 20 | 10 | | | 35 |
| urea peroxide | | 20 | 30 | 20 | |
| sodium magnesium silicate | | | 3 | | |
| silica fine powder | | 2.5 | 2 | | |
| carboxy polymethylene | 3 | 3 | 3 | 3 | 3 |
| sodium hydroxide (pH adjusted) | 0.5 | 0.5 | 0.5 | 0.5 | 0.5 |
| total | 100 | 100 | 100 | 100 | 100 |

<Method of Using>

The following procedures were followed for the application of the aforementioned Examples and Comparative Examples.

(1) A pretreatment is applied to the object teeth in removing dental plaques, dental calculi, and tars on the teeth surface with a supersonic scaler.

(2) The teeth surface was cleaned with a rubber cup or the like by a usual method and dried.

(3) Kept dry by using a rubber dam.

(4) For each of the Examples, the first component was applied on the teeth surface with a brush, let stand for 20 seconds, and then dried with air.

(5) The second component was applied on the teeth surface for each of the Examples shown, while for the Comparative Examples, a dental bleaching agent was applied, or for the viscous ones, attached on the teeth surface. It was then followed by irradiation with a dental visible light irradiator (trade name: Labolight LVII, manufactured by GC Corporation.) for five minutes per irradiation. The distance between the irradiator and the teeth surface was about 1 cm.

(6) At an interval of 10~30 minutes, a fresh dental bleaching agent was applied on and the irradiation was repeated.

(7) For evaluating the effectiveness of the bleaching visually, the dental shade guide (trade name: Luminvacuum, manufactured by Bita Co.) was used as the reference for judging the teeth color, before and after the bleaching, and the color were recorded by a video camera. Thereafter, evaluations by the patients were conducted by viewing the images recorded before and after the bleaching. Table 4 summarized patients' judgments according to the following categories:

TABLE 4

| | site | accumulated irradiation time (minutes) | color shade of teeth before treatment | color shade of teeth after treatment | effects |
|---|---|---|---|---|---|
| Example 1 | maxilla left 1 | 90 | B4 | B2 | +++ |
| Example 2 | maxilla left 2 | 100 | A4 | A2 | +++ |
| Example 3 | maxilla right 1 | 80 | A3.5 | A2 | +++ |
| Example 4 | maxilla left 3 | 90 | A3.5 | A2 | +++ |
| Example 5 | maxilla right 2 | 100 | D4 | D2 | ++ |
| Example 6 | mandible left 1 | 70 | B3 | B1 | +++ |
| Example 7 | mandible left 2 | 65 | B3 | B1 | +++ |
| Example 8 | maxilla right 3 | 80 | A4 | A2 | +++ |
| Example 9 | maxilla right 3 | 90 | B4 | B2 | +++ |
| Example 10 | maxilla left 2 | 80 | C4 | C2 | +++ |
| Example 11 | maxilla right 2 | 120 | A3.5 | A2 | +++ |
| Example 12 | mandible left 3 | 100 | B4 | B2 | +++ |
| Example 13 | mandible left 2 | 90 | C4 | C2 | +++ |
| Example 14 | mandible right 1 | 90 | C4 | C2 | +++ |
| Example 15 | mandible right 2 | 80 | A3.5 | A2 | +++ |
| Example 16 | mandible left 2 | 100 | A4 | A3 | +++ |
| Example 17 | mandible left 1 | 90 | A3.5 | A2 | +++ |
| Example 18 | maxilla left 1 | 120 | A3.5 | A2 | +++ |
| Example 19 | maxilla right 2 | 100 | C4 | C2 | +++ |
| Example 20 | mandible left 1 | 90 | B4 | B2 | ++ |
| Example 21 | mandible left 2 | 60 | B3 | B1 | ++ |
| Example 22 | maxilla right 3 | 60 | A3.5 | A2 | +++ |
| Example 23 | maxilla right 3 | 50 | A3.5 | A2 | +++ |
| Example 24 | maxilla left 2 | 30 | D4 | D2 | +++ |
| Example 25 | maxilla left 2 | 55 | A4 | A2 | +++ |
| Example 26 | mandible right 2 | 65 | B3 | B1 | +++ |
| Example 27 | mandible left 2 | 70 | B4 | B2 | +++ |
| Example 28 | mandible left 1 | 60 | C4 | C2 | +++ |
| Example 29 | maxilla left 1 | 50 | A3.5 | A2 | +++ |
| Example 30 | mandible left 3 | 85 | B3 | B1 | +++ |
| Comparative Example 1 | maxilla right 3 | 100 | A3.5 | A3 | + |
| Comparative Example 2 | mandible right 2 | 65 | B3 | B2 | + |

+++: the patient was greatly satisfied
++: the patient felt somewhat satisfactory about the results of bleaching
+: the patient noticed some effects of bleaching but not satisfied with some remaining discoloration From the foregoing results, it was confirmed that highly whitening results were achieved by using the dental bleaching agent set of the present invention and following the dental bleaching methods of the present invention.

As has been described in detail, the present invention of dental bleaching agent set and the dental bleaching method remove the shortcomings of the conventional bleaching agent that the light is difficult to reach to the powder on the teeth surface where the bleaching action is to take place due to its own sheltering effects of titanium oxide powder, when the external light is to activate the photocatalytic activities of the titanium oxide having photocatalytic activities contained by about 5% therein. The present invention effectively activates the powder having photocatalytic activities for bleaching and thus contributes greatly to the field of whitening teeth.

What is claimed is:

1. A dental bleaching agent kit comprising:
   a first component for applying to a tooth surface comprising an organic solvent containing at least one of a nitrogen doped titanium oxide powder and a titanium oxinitride powder which is photocatalytic in the visible spectral region; and
   a second component for applying to the tooth surface after the first component comprising a compound that produces hydrogen peroxide in water, a thickener, and a carrier.

2. The dental bleaching agent kit as claimed in claim 1, wherein the content of the titanium oxinitride powder is 0.001~30% by weight based on the total weight of the composition.

3. The dental bleaching agent kit as claimed in claim 1, wherein the titanium oxinitride powder has a Ti—O—N structure containing nitrogen in a crystalline lattices.

4. The bleaching agent kit as claimed in claim 1, wherein the at least one of the titanium oxinitride powder and the titanium oxinitride powder carries ceramics on the surface thereof in an island form, an acicular form, or a mesh form.

5. The bleaching agent kit as claimed in claim 3, wherein at least one of the nitrogen doped titanium oxide powder and the titanium oxinitride powder carries a charge separation substance on the surface thereof.

6. The bleaching agent kit as claimed in claim 1, wherein the first component further comprises one or more of a metal oxide, a metal salt, and a metal powder.

7. The bleaching agent kit as claimed in claim 6, wherein the content of one or more of the metal oxide, the metal salt, and the metal powder is 0.001~10% by weight based on the total weight of the composition.

8. The bleaching agent kit as claimed in claim 1, wherein the first component further comprises 0.5~20% by weight of a thickener based on the total weight of the composition.

9. The bleaching agent kit as claimed in claim 1, wherein the first component further comprises water.

10. The bleaching agent kit as claimed in claim 1, wherein at least one of the first component and the second component has a pH value of 5.0~10.0.

11. The bleaching agent kit as claimed in claim 1, wherein the second component consists of 1~40% by weight of the compound that produces hydrogen peroxide in water, 0.5~20% by weight of the thickener, and the balance being the carrier.

12. A dental bleaching method comprising the steps of:
applying, to teeth surface, a first component comprising an organic solvent containing at least one of a, a nitrogen doped titanium oxide powder and a titanium oxinitride powder which is photocatalytic in the visible spectral region; and
applying, to the teeth surface after the first component, a second component comprising a compound that produces hydrogen peroxide in water, a thickener, and a carrier; and irradiating light on the teeth surface.

13. A dental bleaching method comprising the steps of:
applying a first component on teeth surface;
applying, to the teeth surface after the first component, a second component; and
irradiating light on the teeth surface,
wherein the first component comprises an organic solvent containing 0.001~30% by weight based on the total weight of the composition of at least one of, a nitrogen doped titanium oxide powder and a titanium oxinitride powder which is photocatalytic in the visible spectral region, and 0.001~10% by weight based on the total weight of the composition of one or more of a metal oxide, a metal salt and a metal powder; and
wherein the second component comprises 1~40% by weight of a compound that produces hydrogen peroxide in water, 0.5~20% by weight of a thickener, and a carrier.

* * * * *

UNITED STATES PATENT AND TRADEMARK OFFICE
CERTIFICATE OF CORRECTION

PATENT NO. : 7,250,155 B2 Page 1 of 1
APPLICATION NO. : 10/791783
DATED : July 31, 2007
INVENTOR(S) : Shin Yamaguchi et al.

It is certified that error appears in the above-identified patent and that said Letters Patent is hereby corrected as shown below:

On the title page, Item (73), the Assignee information is incorrect. Item (73) should read:

(73) Assignees: GC Corporation, Tokyo (JP):
               Kabushiki Kaisha Toyota Chuo Kenkyusho, Aichi-gun (JP)

Signed and Sealed this

First Day of April, 2008

JON W. DUDAS
*Director of the United States Patent and Trademark Office*